(12) United States Patent
Powers et al.

(10) Patent No.: US 10,926,112 B2
(45) Date of Patent: Feb. 23, 2021

(54) DEVICES AND METHODS FOR THE ULTRASOUND TREATMENT OF ISCHEMIC STROKE

(71) Applicants: BRACCO SUISSE S.A., Manno (CH); KONINKLIJKE PHILIPS N.V., Eindhoven (NL)

(72) Inventors: Jeffry Earl Powers, Bainbridge Island, WA (US); Ralf Seip, Carmel, NY (US); William Tao Shi, Briarcliff Manor, NY (US); Francois Tranquart, Nernier (FR); Yannick Bohren, Renens (CH); Emmanuel Jean-Marie Gaud, La Croix-de-Rozon (CH); Ebeline Bihel, Plan les Quates (CH); Feng Yan, Grand-Lancy (CH); Marcel Arditi, Aire (CH); Jean-Marc Paul Robert Hyvelin, Geneva (CH)

(73) Assignees: KONINKLIJKE PHILIPS N.V., Eindhoven (NL); BRACCO SUISSE SA, Manno (CH)

( * ) Notice: Subject to any disclaimer, the term of this patent is extended or adjusted under 35 U.S.C. 154(b) by 920 days.

(21) Appl. No.: 14/902,012

(22) PCT Filed: Jul. 2, 2014

(86) PCT No.: PCT/EP2014/064052
§ 371 (c)(1),
(2) Date: Dec. 30, 2015

(87) PCT Pub. No.: WO2015/000953
PCT Pub. Date: Jan. 8, 2015

(65) Prior Publication Data
US 2016/0279449 A1  Sep. 29, 2016

Related U.S. Application Data

(60) Provisional application No. 61/842,402, filed on Jul. 3, 2013, provisional application No. 61/842,404, filed on Jul. 3, 2013.

(30) Foreign Application Priority Data

Aug. 28, 2013 (EP) ..................... 13182062

(51) Int. Cl.
*A61N 7/00* (2006.01)
*A61B 8/08* (2006.01)
*A61B 17/22* (2006.01)

(52) U.S. Cl.
CPC .............. *A61N 7/00* (2013.01); *A61B 8/0833* (2013.01); *A61B 17/22004* (2013.01);
(Continued)

(58) Field of Classification Search
CPC ............................ A61N 7/00; A61B 17/22004
See application file for complete search history.

(56) References Cited

U.S. PATENT DOCUMENTS 5,558,092 A    9/1996  Unger et al.
5,686,060 A   11/1997  Schneider et al.
(Continued)

FOREIGN PATENT DOCUMENTS

CN    1792334 A    6/2006
JP    2004033476 A    2/2004
(Continued)

OTHER PUBLICATIONS

Radhakrishnan, K. "Relationship Between Cavitation and Loss of Echogenicity From Ultrasound Contrast Agents" Phys. Med. Biol. vol. 58, No. 18, 2013 pp. 6541-6563.
(Continued)

*Primary Examiner* — Hien N Nguyen

(57) ABSTRACT

Ultrasonic sonothrombolysis systems to produce two acoustic pressure levels of insonation during stroke therapy, mid/high acoustic pressure insonation directed to the site of a blood clot where microbubbles are present to induce
(Continued)

microbubble-mediated blood clot lysis, and low acoustic insonation directed to the region surrounding the site of the blood clot where microbubbles are present to stimulate microvascular reperfusion of the surrounding tissue. The systems simultaneously produce blood clot lysis at the site of an occlusion and stimulate reperfusion of tissue affected by the occlusion.

15 Claims, 8 Drawing Sheets

(52) U.S. Cl.
CPC ............ *A61B 8/483* (2013.01); *A61B 8/5246* (2013.01); *A61B 2017/22007* (2013.01); *A61B 2017/22008* (2013.01); *A61N 2007/0004* (2013.01); *A61N 2007/0039* (2013.01); *A61N 2007/0052* (2013.01); *A61N 2007/0078* (2013.01); *A61N 2007/0086* (2013.01)

(56) References Cited

U.S. PATENT DOCUMENTS

| | | | |
|---|---|---|---|
| 5,711,933 A | 1/1998 | Bichon | |
| 5,997,479 A | 12/1999 | Savord | |
| 6,013,032 A | 1/2000 | Savord | |
| 6,333,021 B1 | 12/2001 | Schneider et al. | |
| 6,530,885 B1 | 3/2003 | Entrekin | |
| 6,623,432 B2 | 9/2003 | Powers et al. | |
| 6,723,050 B2 | 4/2004 | Dow | |
| 2005/0019744 A1 | 1/2005 | Bertuglia | |
| 2006/0052699 A1* | 3/2006 | Angelsen | A61B 8/14 600/437 |
| 2008/0097206 A1 | 4/2008 | Chomas et al. | |
| 2010/0125193 A1* | 5/2010 | Zadicario | A61N 7/02 600/411 |
| 2010/0160780 A1 | 6/2010 | Swan | |
| 2011/0178444 A1 | 7/2011 | Slayton et al. | |
| 2011/0213248 A1 | 9/2011 | Murakami et al. | |
| 2011/0251489 A1 | 10/2011 | Zhang et al. | |
| 2012/0016239 A1* | 1/2012 | Barthe | A61B 8/0858 600/439 |
| 2012/0083718 A1 | 4/2012 | Allenman et al. | |
| 2012/0244078 A1* | 9/2012 | Rychak | A61K 49/0002 424/9.6 |
| 2012/0296241 A1* | 11/2012 | Mishelevich | A61N 7/00 601/2 |

FOREIGN PATENT DOCUMENTS

| | | |
|---|---|---|
| WO | 2004069284 A2 | 8/2004 |
| WO | 2005074805 A1 | 8/2005 |
| WO | 2007058668 A1 | 5/2007 |
| WO | 2008017997 A2 | 2/2008 |
| WO | 2012042423 A1 | 4/2012 |
| WO | 2012042494 A1 | 5/2012 |

OTHER PUBLICATIONS

Vignon et al, "Microbubble Cavitation Imaging" IEEE Trans. Ultrason. Ferroelectr. and Freq. Controls, 60-4 Apr. 2013, p. 661-670.

Balucani et al "Ultrasound and Microspheres-Enhanced Thrombolysis for Stroke Treatment" Current Cardiology Reports. vol. 12, No. 1, Jan. 1, 2010 p. 34-41.

Database Medline ; U.S. National Library of Med. Bethesda, MD, Sep. 2005 Bertuglia "Increase in Capillary Perfusion Following Low-Intensity Ultrasound and Microbubbles During Postischemic Reperfusion".

* cited by examiner

DEVICES AND METHODS FOR THE ULTRASOUND TREATMENT OF ISCHEMIC STROKE

This application is the U.S. National Phase application under 35 U.S.C. § 371 of International Application No. PCT/EP2014/064052, filed on Jul. 2, 2014, which claims the benefit of US Application Nos. 61/842,402 filed on Jul. 3, 2013; 61/842,404 filed Jul. 3, 2013 and EP13182062.3 filed Aug. 28, 2013. These applications are hereby incorporated by reference herein.

This invention relates to medical ultrasound systems and, in particular, to ultrasound systems which, in combination with vascular acoustic resonators, perform therapy for stroke victims.

Ischemic stroke is one of the most debilitating disorders known to medicine. The blockage of the flow of blood to the brain can rapidly result in paralysis or death. Attempts to achieve recanalization through thrombolytic drug therapy such as treatment with tissue plasminogen activator (tPA) has been reported to cause symptomatic intracerebral hemorrhage in a number of cases. Advances in the diagnosis and treatment of this crippling affliction are the subject of continuing medical research.

Use of ultrasound waves is an emerging non-invasive stroke treatment modality which is applied to help lyse blood clots causing vascular occlusion. According to certain treatments, gas-filled microvesicles or other vascular acoustic resonators (VARs) are systemically injected into the blood stream. The oscillation of the VARs in the ultrasound field helps disrupt the blood clots that cause heart attacks and stroke. These ultrasound-based treatments are also known in the art as sonothrombolysis or sonolysis. Recent studies have shown, however, that removal of the clot may not always restore nourishing blood flow to affected tissues. Furthermore, the present inventors have observed that, even when the clot continues to occlude the artery which is the source of blood flow to cells and tissue, ultrasound may nonetheless have a beneficial effect. The physiological properties behind these effects are not fully understood. Others have speculated that even when the clot is dissolved or broken up, capillaries of the vascular structure downstream from the location of the clot may still be occluded, possibly by microclots, small particles of fibrous material that may have preceded the clot or broken off from the clot and continue to block the flow of blood to the microvasculature. Others have also speculated that the microvasculature is occluded by neutrophils, white blood cells that have been stimulated by the ischemic condition to rush to the microvasculature as the body's response to the trauma, where they end up occluding the microvasculature. Still others have surmised that microvascular structures may be supplied with blood by paths from collateral arteries, so that some oxygenated blood may reach an ischemic region from alternate sources even when the major arterial conduit remains blocked. Regardless of the actual explanation of the underlying phenomena and their interplay, it is desirable to provide treatment of the occlusion in the major artery to provide the desired recanalization while concurrently promoting the flow of blood to affected microvasculature surrounding the occlusion to provide reperfusion of the capillary bed.

Furthermore, sonothrombolysis is an emerging non-invasive stroke treatment modality in which systemically injected VARs are insonified, and their resultant oscillation or rupture is used to lyse the clot causing the occlusion in acute ischemic stroke. Sonothrombolysis uses VARs oscillating in an ultrasound field to disrupt the blood clots that cause heart attacks and stroke. But there is an inherent problem in this treatment procedure, which is delivering a continuing flow of VARs to the site of the vascular obstruction. Since the clot is obstructing the flow in the vessel, the clot itself is compromising the delivery of new VARs to the site of the obstruction, and downstream from it. The greater the degree of flow obstruction, the smaller the supply of fresh VARs-containing blood to the clot. Accordingly it is desirable to be able to promote the flow of new VARs to the site of the clot despite the obstruction of the blood supply by the clot to facilitate enhanced interactions between the resonators and the clot to promote clot lysis.

SUMMARY OF THE INVENTION

In accordance with an aspect of the present invention, an ultrasound stroke treatment system comprises a transducer which is capable of targeting an occlusion in the presence of vascular acoustic resonators (VARs) by applying ultrasound waves at mid- or high-acoustic pressure levels to promote clot lysis and vessel recanalization, and applying ultrasound waves at lower acoustic pressure levels over a wider area surrounding the occlusion to promote microvascular reperfusion in the surrounding area in the presence of VARs. The applications of lower and higher ultrasound pressure may be activated simultaneously or in a time-interleaved manner. For example, mid/high acoustic pressures can be directed to a site of an occlusion during a therapy time interval and low acoustic pressures can be directed to a region surrounding the site of the occlusion during a reperfusion stimulation time interval. In an embodiment of the invention, the transmit controller may be configured to step ultrasound waves (e.g. by sequential pulses) at low acoustic pressure levels around the region surrounding the site of the occlusion. The transducer may be an electronically steered two- or one-dimensional array or a single-element ultrasound transducer mechanically steered for this purpose. Preferably the higher pressure (and optionally also the lower pressure) therapy mode is periodically interrupted to allow time for an infusion of fresh VARs to the site of the treatment, during which imaging may be performed to visualize the site of the treatment and maintain accurate targeting of the clot. The VARs act as oscillating bodies when subjected to ultrasound waves, thus causing minute displacements (strain) at a microscopic level that promote recanalization or reperfusion within vascular or microvascular structures.

In accordance with a further aspect of the present invention a therapeutic method of treating ischemic stroke is described which promotes clot lysis and vessel recanalization at a site of a vascular occlusion and concurrently promotes microvascular reperfusion in the area surrounding said occlusion. The method comprises administering a VAR composition to a subject; controlling an array transducer to direct ultrasound waves at mid- or high-acoustic pressure levels to the site of occlusion where VARs are present to stimulate clot lysis at the site; and controlling an array transducer to direct ultrasound waves at low acoustic pressure levels to a region surrounding the site of the occlusion to stimulate microvascular reperfusion.

In accordance with yet a further aspect of the present invention, an ultrasonic sonothrombolysis system for ischemic stroke therapy has two ultrasonic array transducers, one acoustically coupled to the ipsilateral, or the side of the head which contains the clot, and the other acoustically coupled to the contralateral (opposite) side of the head. The contralateral transducer delivers very low to low acoustic pressure that produces an acoustic radiation force which pushes new acoustic resonators toward the vascular occlusion while the ipsilateral transducer delivers mid- or high-intensity ultrasonic energy that vibrates or ruptures resonators at the site of the occlusion to break up the obstructing thrombus. The supply of resonators to the obstruction is enhanced by acoustic radiation from the contralateral transducer while the ipsilateral transducer, which is in closer proximity to the obstruction, delivers the therapeutic energy to break up the obstruction.

FIGURES

DESCRIPTION

Figure 1:
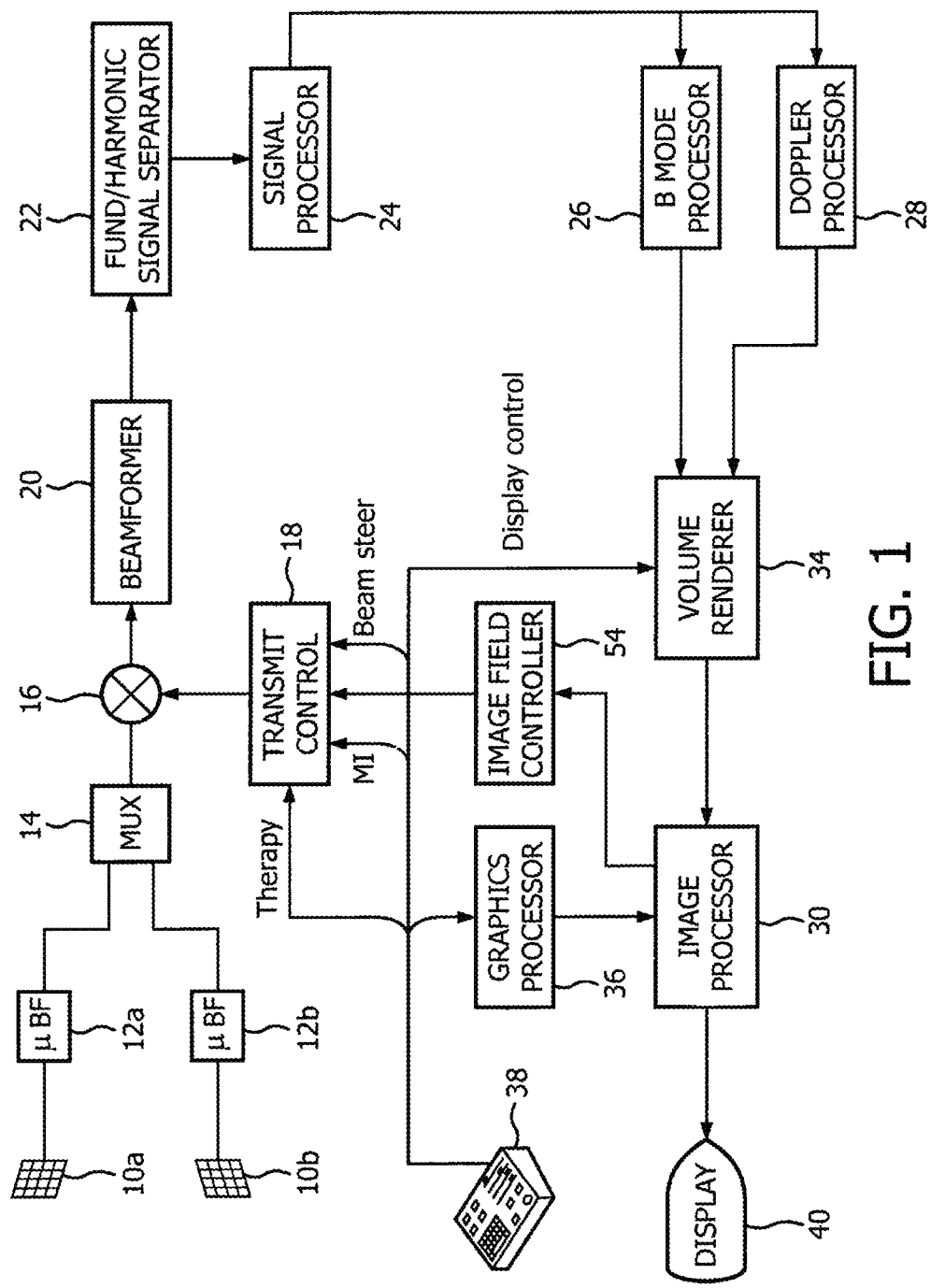
FIG. 1 illustrates in block diagram form an ultrasonic diagnostic imaging system constructed in accordance with the principles of the present invention.

Referring first to FIG. 1, an ultrasound system constructed in accordance with the principles of the present invention is shown in block diagram form. Two transducer arrays 10a and 10b are provided for transmitting ultrasonic waves and receiving echo information. In this example the arrays shown are two dimensional arrays of transducer elements capable of providing 3D image information although an implementation of the present invention may also use one dimensional arrays of transducer elements which can be used to produce 2D (planar) images and/or deliver ultrasonic energy to a region of interest. Another alternative is to mechanically steer a one-dimensional array to produce the effect of an electronically steered 1D or 2D array. The transducer arrays in this implementation are coupled to microbeamformers 12a and 12b which control transmission and reception of signals by the array elements and in particular the steering and focusing of ultrasonic beams for imaging and therapy. Microbeamformers are capable of at least partial beamforming of the signals received by groups or "patches" of transducer elements as described in U.S. Pat. No. 5,997,479 (Savord et al.), U.S. Pat. No. 6,013,032 (Savord), and U.S. Pat. No. 6,623,432 (Powers et al.). Signals are routed to and from the microbeamformers by a multiplexer 14 by time-interleaved signals. Other implementations may require higher power transmit signals for therapy than those produced by a microbeamformer, in which case transducer drive circuitry capable of higher output power levels may be employed. The multiplexer is coupled to a transmit/receive (T/R) switch 16 which switches between transmission and reception and protects sensitive input circuitry of the main beamformer 20 from high amplitude transmit signals. The transmission of ultrasonic beams from the transducer arrays 10a and 10b under control of the microbeamformers 12a and 12b or other drive circuitry is directed by the transmit controller 18 coupled to the T/R switch, which receives input from the user's operation of the user interface or control panel 38.

The partially beamformed echo signals produced by the microbeamformers 12a, 12b are coupled to a main beamformer 20 where partially beamformed signals from the individual patches of elements are combined into a fully beamformed signal. For example, the main beamformer 20 may have 128 channels, each of which receives a partially beamformed signal from a patch of 12 transducer elements. In this way the signals received by over 1500 transducer elements of a one- or two-dimensional array can contribute efficiently to a single beamformed signal.

The beamformed signals are coupled to a nonlinear echo processor (or fundamental/harmonic signal separator) 22. The processor (or separator) 22 acts to separate (linear) echo signals arising from tissue structures from those (nonlinear) arising from VARs, thus enabling the identification of the strongly non linear echo signals returned from VARs. The processor 22 may operate in a variety of ways such as by bandpass filtering the received signals in fundamental frequency and harmonic frequency bands, or by processes known as pulse inversion harmonic separation, or power-modulation, which are also able to cancel tissue echoes while preserving VAR echoes, even in the fundamental band. Signal separators can be used to distinguish between linear and non-linear signals or fundamental and harmonic signals. A suitable nonlinear/linear signal separator is shown and described in international patent publication WO 2005/074805 (Bruce et al.). The separated signals are coupled to a signal processor 24 where they may undergo additional enhancement such as speckle removal, signal compounding, and noise elimination.

The processed signals are coupled to a B mode processor 26 and a Doppler processor 28. The B mode processor 26 employs amplitude detection for the imaging of structures in the body such as muscle, organs or tissue. B mode images of structure of the body may be formed in either the nonlinear mode or the linear mode. Tissues in the body and VARs both return both types of signals and the relatively strong nonlinear returns of VARs enable VARs to be clearly segmented in an image in most applications. The Doppler processor processes temporally distinct signals from tissue and blood flow for the detection of motion of substances in the image field including VARs. The structural and motion signals produced by these processors are scan converted and coupled to a volume renderer 34, which produces image data of tissue structure, flow, or a combined image of both characteristics. The volume renderer 34 will convert a 3D data set into a projected 3D image as viewed from a given reference point as described in U.S. Pat. No. 6,530,885 (Entrekin et al.) As described therein, when the reference point of the rendering is changed the 3D image can appear to rotate in what is known as kinetic parallax. This image manipulation is controlled by the user as indicated by the Display Control line between the user interface 38 and the volume renderer 34. Also described by Entrekin et al. is the representation of a 3D volume by planar images of different image planes, a technique known as multiplanar reformatting (MPR). The volume renderer 34 can operate on image data in either rectilinear or polar coordinates as described in U.S. Pat. No. 6,723,050 (Dow et al.) The 2D or 3D images are coupled from the volume renderer to an image processor 30 for further enhancement, buffering and temporary storage for display of static or live 2D MPR or 3D images on an image display 40.

A graphics processor 36 is coupled to the image processor 30 which generates graphic overlays for display with the ultrasound images. These graphic overlays can contain standard identifying information such as patient name, date and time of the image, imaging parameters, and the like, and can also produce a graphic overlay of a therapy beam vector steered by the user as described below. For this purpose the graphics processor receives input from the user interface 38. The user interface is also coupled to the transmit controller 18 to control the generation of ultrasound signals from the transducer arrays 10a and 10b in the therapy and imaging modes and hence the images produced by and therapy applied by the transducer arrays. The transmit parameters controlled in response to user adjustment include the MI (Mechanical Index) which controls the peak intensity of the transmitted waves, which is related to the acoustic pressure and cavitational effects of the ultrasounds, steering of the transmitted beams for image positioning and/or steering of a therapy beam as discussed below. A therapy control signal commands the transmit controller to operate the transducer array in the therapy or diagnostic imaging mode as described below.

The transducer arrays 10a and 10b transmit ultrasonic waves into the cranium of a patient from one or both sides of the head, although other locations may also or alternately be employed such as the front of the head or the sub-occipital acoustic window at the back of the skull. The sides of the head of most patients advantageously provide suitable acoustic windows for transcranial ultrasound at the temporal bones around and in front of the ears on either side of the head. In order to transmit and receive echoes through these acoustic windows the transducer arrays must be in good acoustic contact at these locations which may be done by holding the transducer arrays in acoustic coupling contact against the head with a headset. Suitable headsets for cranial ultrasound transducers are described in international patent publication no WO 2008/017997 (Browning et al.), US pat. pub. no. US 2012/0083718 (Alleman et al.), and US pat. pub. no. US 2011/0251489 (Zhang et al.), for instance.

In accordance with the principles of the present invention, the ultrasound system of FIG. 1 is used to apply two types of VAR-mediated ultrasound therapy concurrently, high acoustic pressure therapy directed at an occlusion to promote the lysis of a blood clot and low acoustic pressure therapy which provides beneficial effects to surrounding microvasculature, the latter being directed to promote microvascular reperfusion. An implementation of the present invention provides a means for achieving a recanalization of occluded major feeding arteries such as the MCA as well as reperfusion of the microvasculature surrounding the occlusion.

Different acoustic-pressure levels will stimulate VAR activity in different ways. Typically, these ranges of pressure levels are differentiated, for each VAR type and size, at a given frequency, and by the nature of acoustic response from the VARs when exposed to these acoustic stimulations. Different thresholds exist which are useful in the determination of these ranges. These thresholds are determined by the appearance of certain frequency components in spectra of echoes scattered by the VARS. A first very low threshold exists, below which VARs only experience negligible oscillation. Below this threshold VAR oscillations are very small and have no therapeutic benefit for stroke treatment. At such very low acoustic pressures, the VARs are not disrupted, their echo spectra do not contain sub-harmonic or ultra-harmonic components (i.e., odd multiples of the sub-harmonic frequency) and VARs can remain present within the ultrasound beam for a long time. A second low threshold can be identified, above which echo signals from VARs start exhibiting sub-harmonic and ultra-harmonic components in their frequency spectra. Above the second threshold, the regime is sometimes referred to as stable cavitation, and will be referred to here as mid acoustic pressure. At these levels, VARs may gradually disappear from the region under ultrasound exposure due to gradual escape of the gas from the VARs' envelope. At acoustic pressure between said very low and low thresholds, VAR oscillations are relatively small but have been shown to promote reperfusion and thus to offer some therapeutic benefits. A third threshold exists, characterized by the appearance of broadband noise within the frequency spectra of echo signals from VARs, above which VARs exhibit inertial cavitation. These frequency components, which may be measured in frequency bands outside multiples of the fundamental and sub-harmonic frequencies, are associated with more rapid disappearance of the VARs. The onset of inertial cavitation is associated with a rupture of VAR envelopes, where the gas body liberated continues to oscillate in response to ultrasound wave, for a duration determined by the dissolution time of the gas in the surrounding medium. These levels are referred to herein as high acoustic pressure levels. Methods for determining thresholds of stable and inertial cavitation, applicable either in vitro or in vivo are known, and described, e.g., in Radhakrishnan, K. et al., "Relationship between cavitation and loss of echogenicity from ultrasound contrast agents," Phys. Med. Biol., Vol. 58, No. 18, 2013, pp. 6541-6563, and Vignon et al. *Microbubble Cavitation Imaging, IEEE Trans. Ultrason., Ferroelectr. and Freq. Controls,* 60-4, April 2013, p 661-670, as well as in patent application WO 2012042423 A1, Monitoring and control of microbubble cavitation in therapeutic ultrasound, Powers JE et al. (2010), each of which is incorporated by reference herein.

Typically, for VARs with a size distribution of approximately 1.5 micrometer in mean (number-average) diameter, stabilized by a phospholipid shell, when measured in plasma at a frequency of about 1 MHz, very low acoustic pressures are less than approximately 80 kPa, low acoustic pressures are between approximately 80 and 140 kPa, mid acoustic pressures are between approximately 140 and 250 kPa, and high acoustic pressures are above approximately 250 kPa.

In some embodiments, the acoustic pressure levels applied to induce a response can be determined in relation to a tissue (e.g., lesion) volume of roughly spherical shape, with a radius r. Certain dimensions, for example, can be estimated for an infarct region in which low acoustic pressure levels are provided to promote reperfusion. In some embodiments, the infarct volume can range from about 10 to 200 $cm^3$, or from about 20 to 100 $cm^3$, or from about 40 to 60 $cm^3$. In one example, the infarct volume can have minimal, nominal, and maximal dimensions of 10, 50, and 200 $cm^3$, respectively. A diameter of the area to be treated can range from about 2.5 to 7.5 cm, or from about 3.5 to 6.5 cm, or from about 4.5 to 5.5 cm. Tn one example, the diameter can have minimal, nominal, and maximal dimensions of 2.7, 4.6, and 7.3 cm, respectively. An area to be treated can range from about 5.5 to 42 $cm^2$, or from about 10 to 30 $cm^2$, or from about 15 to 20 $cm^2$. In one example, the area can have minimal, nominal, and maximal dimensions of 5.6, 16.4, and 41.3 cm², respectively. For promoting recanalization of an occluded region with mid/high acoustic pressure, different dimensions can be used. For example, a diameter of a region with an occlusion can range from about 0.2 to 2 cm, or from about 0.5 to 1.5 cm, or from about 0.7 to 1.1 cm. In one example, the diameter can have minimal, nominal, and maximal dimensions of 0.2, 0.8, and 2 cm, respectively. The area to be treated can range from about 0.03 to about 3.1 cm², or from about 0.3 to 2 cm², or from about 0.7 to 1.2 cm². In one example, the area can have minimal, nominal, and maximal dimensions of 0.03, 0.5, and 3.1 cm², respectively. Ranges for treatment time can also be optimized for a given treatment application. For example, for the above scenario, treatment duration can range from about 15 to 120 minutes, or from about 30 to 90 minutes, or from about 45 to 75 minutes. In one example, the treatment duration can be a minimal, nominal or maximal duration of 15, 60, or 120 minutes, respectively. Pulse durations for the mid/high acoustic pressure can be a minimal, nominal or maximal duration of 0.01, 20, or 500 milliseconds, respectively. Pulse durations for the low acoustic pressure can range from about 0.01 to about 10000 milliseconds, from about 100 to about 5000 milliseconds, or from about 750 to 2500 milliseconds. In one example, the pulse duration can be a minimal, nominal or maximal duration of 0.01, 1000, or 10000 milliseconds, respectively. There may also be an off-time for replenishment ranging from minimally greater than 0 to 20 seconds, or from about 2 to 15 seconds, or from about 4 to 10 seconds. In one example, the time for replenishment can be minimally greater than 0 seconds, nominally 5 seconds, and maximally 20 seconds. Preferred treatment duration can range from about 30 to 90 minutes, or from about 45 to 75 minutes, or from about 55 to 65 minutes. In one example, the treatment duration can be a minimal, nominal or maximal duration of 30, 60, or 90 minutes, respectively. Pulse durations for the mid/high acoustic pressure can range from about 0.1 to 100 milliseconds, or from about 5 to 50 milliseconds, or from about 15 to 35 milliseconds. In one example, the pulse duration for the mid/high acoustic pressure can be a minimal, nominal or maximal duration of 0.1, 20, or 100 milliseconds, respectively. Pulse durations for the low acoustic pressure can range from about 1 to 5000 milliseconds, from about 300 to 2500 milliseconds, or from about 500 to 1500 milliseconds. In one example, pulse duration for the low acoustic pressure can be a minimal, nominal or maximal duration of 1, 1000, or 5000 milliseconds, respectively. There may also be an off-time for replenishment ranging from about 1 to 10 seconds, or from about 2 to 8 seconds, or from about 3 to 6 seconds. In one example, an off-time for replenishment can be minimally greater than 1 seconds, nominally 5 seconds, and maximally 10 seconds. It is further noted that any duration times and/or dimensions between the minimal and maximal value described above can also be selected for a given treatment.

According to an aspect of the invention, the system as above defined includes VARs, which operate in combination with the transducer of the system when submitted to the applied ultrasound waves at the required acoustic pressures. Vascular acoustic resonators include any component capable of converting acoustic pressure in a propagation-medium into micron-size displacements, capable of applying strain onto blood clots or vessel walls, also with micron-size deformation amplitude. Examples of suitable VARs include gas-filled microvesicles, i.e. vesicles of nano- or micron-size comprising a stabilizing envelope containing a suitable gas therein. The formulation and preparation of VARs is well known to those skilled in the art, including, for instance, formulation and preparation of: microbubbles with an envelope comprising a phospholipid, as described e.g. in WO 91/15244, U.S. Pat. No. 5,686,060 (Schneider et al.) or WO 2004/069284; microballoons with an envelope comprising a polymer, as described e.g. in U.S. Pat. No. 5,711,933; or microcapsules with an envelope comprising a biodegradable water insoluble lipid, as described e.g. in U.S. Pat. No. 6,333,021. Preferably, the stabilizing envelope comprises an amphiphilic material, more preferably a phospholipid. Preferred phospholipids include esters of glycerol with one or preferably two (equal or different) residues of fatty acids and with phosphoric acid, wherein the phosphoric acid residue is in turn bound to a hydrophilic group. Other preferred phospholipids include phosphatidic acids, i.e. the diesters of glycerol-phosphoric acid with fatty acids. Particularly preferred phospholipids are fatty acids diesters of phosphatidylcholine, ethylphosphatidylcholine, phosphatidylglycerol, phosphatidic acid, phosphatidylethanolamine, phosphatidylserine, phosphatidylinositol or of sphingomyelin. Polymer-modified phospholipids, including pegylated phospholipids, can also be advantageously employed for forming the stabilizing envelope of microbubbles. Any biocompatible gas, gas precursor or mixture thereof may be employed to fill the above microvesicles. Fluorinated gases are preferred, in particular perfluorinated gases. Particularly preferred gases are $SF_6$, $C_3F_8$, $C_4F_{10}$ or mixtures thereof, optionally in admixture with air, oxygen, nitrogen, carbon dioxide or mixtures thereof, as described for instance in U.S. Pat. Nos. 6,881,397 or 5,556,610.

The components forming the stabilizing envelope of the VARs, optionally in admixture with other excipients, can be stored as a dry residue in contact with the desired gas(es). Microvesicles are typically prepared by contacting the dry residue in the presence of the gas(es) with an aqueous carrier (e.g., saline or glucose solution) under gentle shaking, thus obtaining an aqueous suspension of microvesicles. The microvesicle suspension is then typically administered by injection, preferably intravenously.

It has been found to be beneficial to limit the application of ultrasound at levels needed to lyse an occluding clot to its location, while insonifying the surrounding brain (or tissue) at lower levels. This way of combining low and mid/high acoustic pressure conditions allows the preservation of VARs in the surrounding tissue, as the disappearance rate of the VARs is relatively low at the lower ultrasound exposure levels. At lower levels, the microstructures can be continually insonified without any substantial disruption thereof, which will maximize the potential for microvascular reperfusion. This balance between ultrasound exposure levels at the site of the occlusion and in surrounding tissue allows for the promotion of both vessel recanalization and microvascular reperfusion. The preferred method of the present invention further provides an interval for allowing replenishment of fresh VARs at the site of the occlusion following their rapid disappearance when subjected to the ultrasound waves at mid/high-pressure and thus optimizes the efficacy of ultrasound treatment and enables visualization of the treatment site to be updated. In a preferred implementation a 2D array transducer is used to electronically steer therapy and imaging beams to the site of the occlusion and over the surrounding volumetric region and to image the therapy site in both two and three dimensions.

The VAR mediation can be provided by a systemically infused dose of a VAR such as gas-filled microvesicles, preferably gas-filled and having a phospholipid-based stabilizing envelope, circulating throughout the entire blood stream and capable of reaching the region to be treated via residual and collateral flow. VARs can be either continuously infused, or delivered via one or multiple bolus injections, which can be administered before and/or in the course of the ultrasound insonation.

A priori knowledge of the microstructure characterization data, which would at a minimum include the ultrasonic pressure thresholds at which the infused microstructures oscillate and cavitate stably and at which they undergo inertial cavitation, together with a parameter which characterizes the VAR lifetime in the bloodstream, will enable the treatment to be effectively initiated and controlled. Knowledge of systemic VAR concentrations (i.e., in terms of numbers of VARs/ml of blood) during bolus injection and infusion may also be required so as to make sure that a minimum required concentration is present in the target region for adequate lysis and microvascular reperfusion. These parameters can be determined empirically in vitro for different VARs and/or different parameters of insonation.

Treatment methods can be formulated which (i) target the main occlusion with the ultrasound beam at mid/high-pressure levels during a certain amount of time during the treatment, (ii) target the surrounding volume with ultrasound waves at low pressure levels during a certain amount of time during the treatment, and (iii) stop the application of therapeutic ultrasound completely for a certain amount of time to permit an influx of fresh VARs for imaging and further therapy. Specific details of exemplary treatment procedures are described below.

A cavitation detector and monitor as described in international patent pub. no. WO 2012/042494 (Vignon et al.) can be used to monitor VAR oscillation in the target region, to non-invasively determine if the VARs are oscillating dominantly in their required mode (i.e., stable cavitation, inertial cavitation, etc.) and to adjust the ultrasound exposure correspondingly if they are not. Ultrasound imaging (operating at a very low acoustic pressure which causes no VAR destruction) is preferably employed to image VAR reperfusion during pauses in the treatment, to observe the progress of clot lysis, and to observe the presence and flow of VARs to the site of the occlusion and surrounding microvasculature. Therapeutic ultrasound exposure is resumed once a sufficiently high amount of VARs have re-perfused the target region after VAR destruction during the higher level ultrasound exposure.

Figure 2:
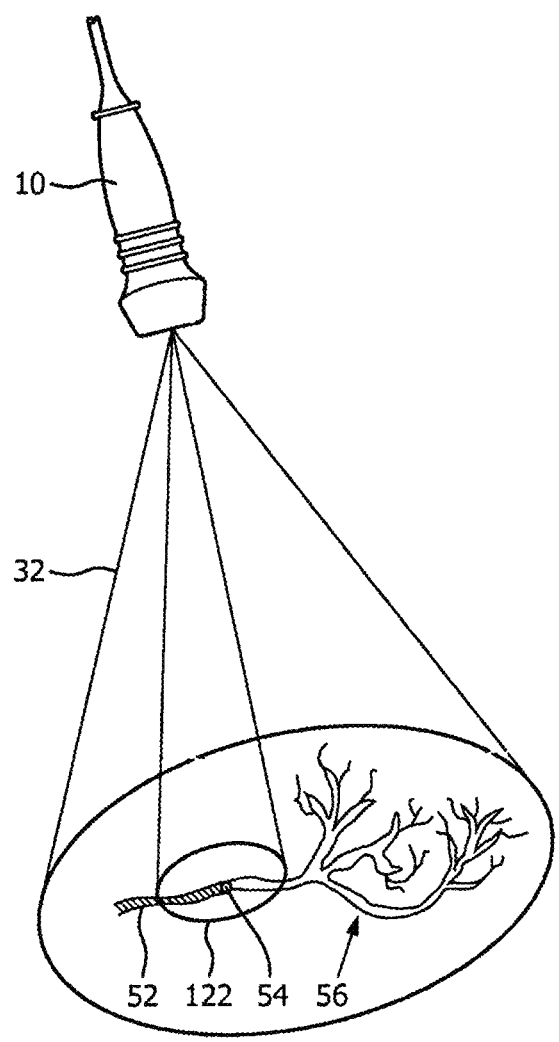
FIG. 2 illustrates the steering of a high pressure ultrasound beam to a blood clot and low pressure insonation of downstream microvasculature in accordance with the principles of the present invention.
Figure 3A:
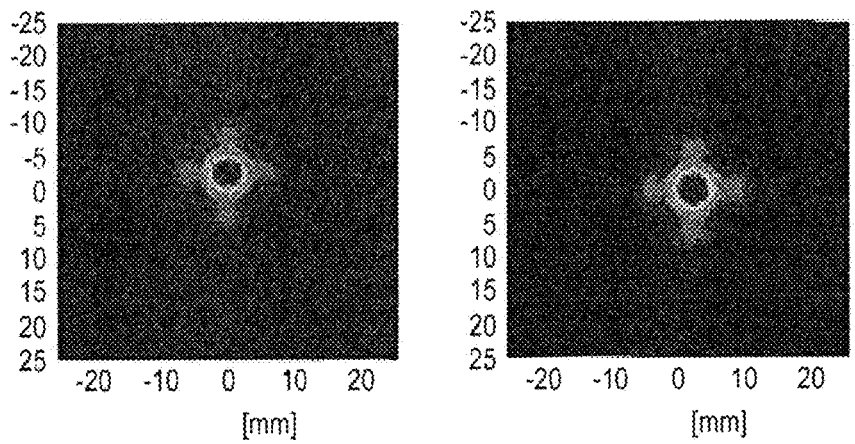
FIGS. 3a-3d illustrate the spatial steering and pulsing of high and low pressure ultrasound beams in accordance with the present invention.
Figure 3B:
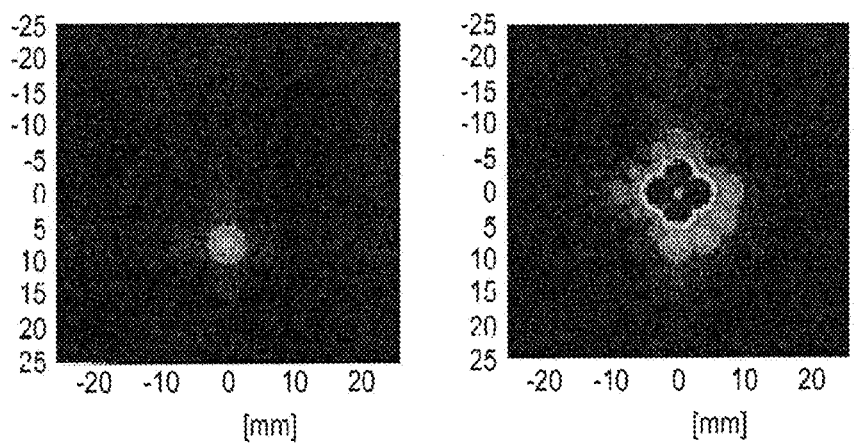
Figure 3C:
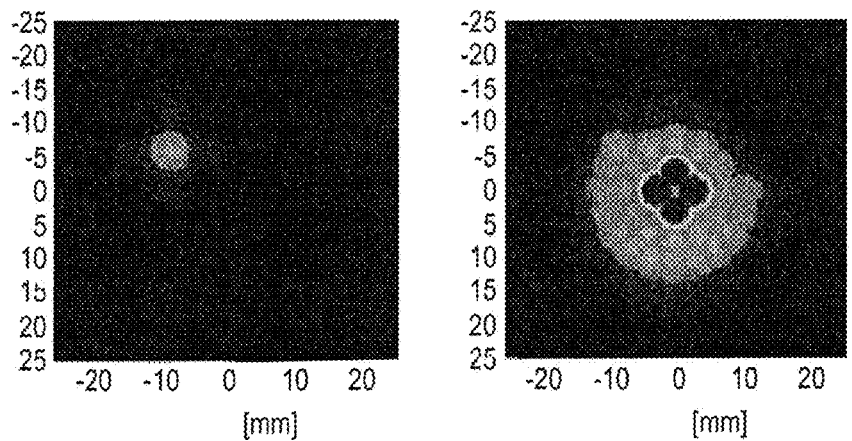
Figure 3D:
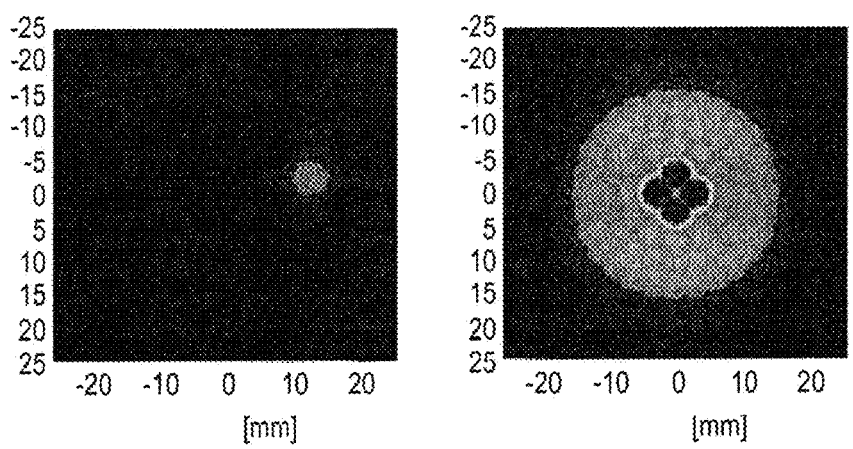

FIG. 2 illustrates an ultrasound probe producing dual therapy levels of ultrasound pressure in accordance with the present invention. Shown projecting from the probe 10 are outlines of two regions 32 and 122 of volumetric ultrasound insonation. The inner conical region 122 is a region in which ultrasound waves with mid- or high-level acoustic pressure are applied to produce cavitation at a site 54 of a blood clot which is occluding a vessel 52. The blood supply is blocked by the occlusion 54 as indicated by the cross-hatched supply portion of the vessel 52. The acoustic pressure in the region 122 may be high enough to produce inertial cavitation of the VARs in the vessel adjacent to the occlusion. Downstream from the occluded blood vessel 52 is microvasculature indicated at 56 which is supplied with blood from the vessel 52, in normal blood flow conditions, or via other collateral paths. This microvasculature in the tissue surrounding the occluded blood vessel is subjected to low acoustic pressure in region 32 by the probe 10, which allows the maintenance of a substantial amount of intact VARs in the microvasculature at the site of treatment. It is the application of this low acoustic pressure in combination with the VARs which is intended to promote microvasculature reperfusion as the higher acoustic pressure of the inner region 122 in combination with the VARs promotes lysis of the blood clot 54. In some embodiments, the dual therapy levels (e.g., mid/high and low acoustic pressures) can be delivered at different time intervals. For example, a transmit controller in the ultrasound system and coupled to control the transmission of ultrasound by the array transducer can be configured (1) to direct ultrasound waves at mid/high acoustic pressure to the site of an occlusion during a first therapy time interval and (2) to direct ultrasound waves at low acoustic pressure levels to a region surrounding the site of the occlusion during a second reperfusion stimulation time interval. Methods of the present invention can include, for example, controlling an array transducer to direct an ultrasound wave at mid/high acoustic pressure to the site of an occlusion where VARs are present to stimulate clot lysis at the site during a first therapy time interval, and controlling an array transducer to direct an ultrasound wave at a low acoustic pressure to a region surrounding the site of the occlusion to stimulate microvascular reperfusion during a stimulation time interval. A peak acoustic pressure transmitted during the first therapy time interval can be greater than a peak acoustic pressure transmitted during the second reperfusion stimulation time interval.

Figure 4:
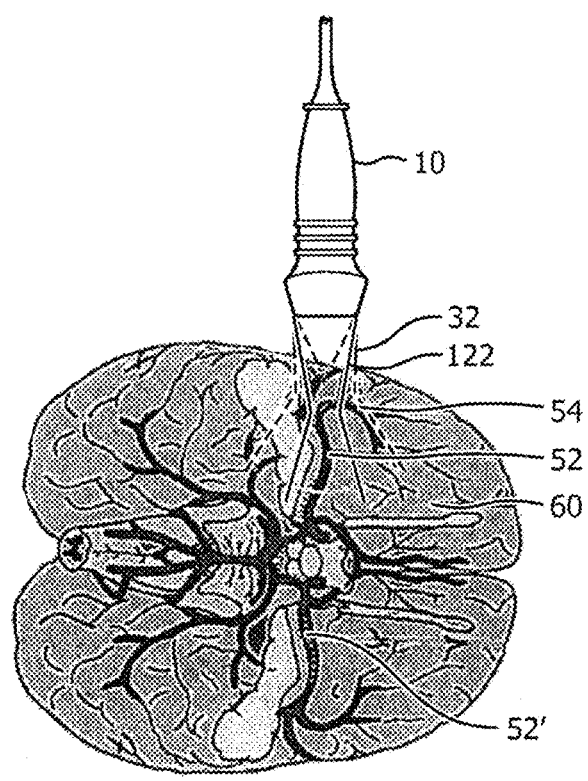
FIG. 4 is an anatomical illustration of treatment of an occlusion in the middle cerebral artery (MCA) of the brain in accordance with the present invention.

FIG. 4 is an anatomical illustration of the dual acoustic pressure therapy technique of the present invention. The probe 10 is seen located at the acoustic window of the temple of the head where it insonifies the brain 60 from the ipsi- or contra-lateral side of the occlusion. The narrow hourglass-shaped profile 122 of high pressure is seen to be focused at the depth of a blood clot 54 in the middle cerebral artery (MCA) 52. The broader dashed line profile 32 delineates the region in which low pressure insonation is provided to the surrounding microvasculature of the brain. The MCA 52' on the other side of the brain is illustrated as containing a continuous flow of VARs in the bloodstream, indicated by the small white dots in the drawing. As low level ultrasound pressure is directed within the profile 32 at the volume surrounding the clot 54, it should be low enough to avoid bubble disappearance during the insonation of each low-pressure ultrasound pulse train if possible. Then, periodically, a mid-pressure pulse train is aimed at the presumed location of the blood clot 54 itself, in the profile 122, in an attempt to erode the clot. The ultrasound beam can cover the necessary region of interest by moving it mechanically and/or electronically, defocusing it into a broader beam, or both. The same probe 10 can further be used for diagnosis by incorporating both transmit and receive capabilities for imaging or Doppler processing. The clot can be located through imaging, and clot lysis and perfusion evaluated by imaging the same VARs as are used for therapy.

Figure 6:
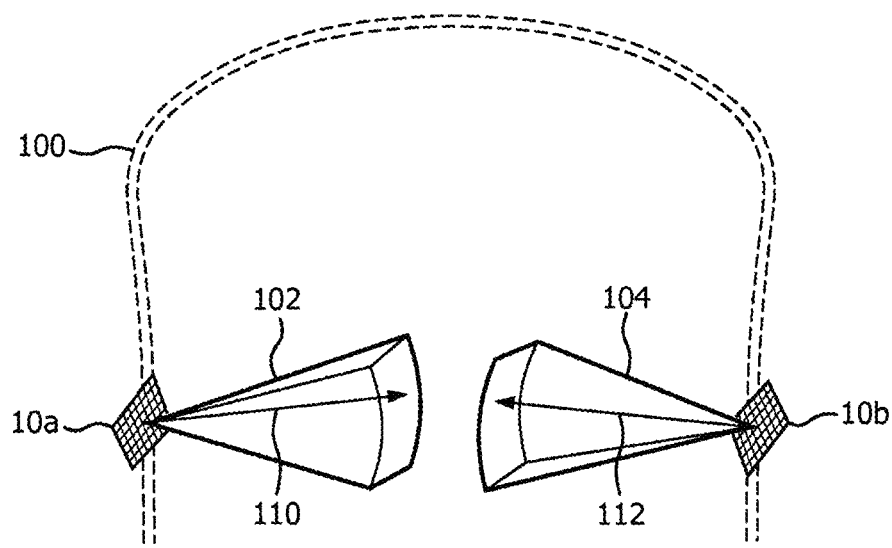
FIG. 6 illustrates stroke treatment with a two-transducer headset in accordance with the present invention.

For stroke treatment the transducer array 10*a*, 10*b* is preferably not employed in a conventional ultrasound probe as shown in FIGS. 2 and 4, but is built into a headset and placed on the temporal bone window of a stroke victim as shown in FIG. 6. Preferably two transducer arrays are used so that the headset will position them against the temporal bone acoustic windows on both sides of the skull 100. When positioned this way, the acoustic fields of the arrays are generally oriented towards the MCA region of the brain and a clot can be treated on either side of the brain, using the array located on the ipsi- and/or on the contra-lateral side of the occlusion to be treated. In this drawing the low pressure regions of the arrays are indicated by regions 102 and 104, and the arrows 110 and 112 indicate the mid/high pressure beam regions which are aimed at an occlusion. In practice of the method of the present invention VARs would be administered intravenously and the location of the clot would be determined by MR, CT, or ultrasound. When the same transducer array 10a, 10b is used for diagnosis and therapy it can be used to locate the clot itself via the absence of blood flow and/or perfusion distal to the site of the clot occlusion, using low-MI ultrasound contrast imaging or Doppler techniques already known. The mid/high-pressure beams produced by the 2D matrix array transducer (a two-dimensional array transducer with attached microbeamformer or driven by high power drive circuitry) is then aimed at the general clot location and the lower pressure microvascular reperfusion beams flood the surrounding volumetric region at risk. Typical penetration distance requirements are approximately 3-10 cm from the skull surface. Typical 3D beam steering angle requirements are approximately up to ±27°, and focal zone size requirements are approximately 5-10 mm in diameter. The ultrasonic output of the array transducer should be sufficient to generate both mid-pressure and low-pressure pulses inside the brain, further accounting for temporal bone attenuation, which attenuates the beam by approximately 75%. In an implementation of the present invention operating at 1 MHz, an in-situ pressure of more than 140 kPa is needed for a phospholipid-based gas-filled microbubble to sustain stable cavitation in the brain, and more than 250 kPa is needed to achieve inertial cavitation.

Figure 7:
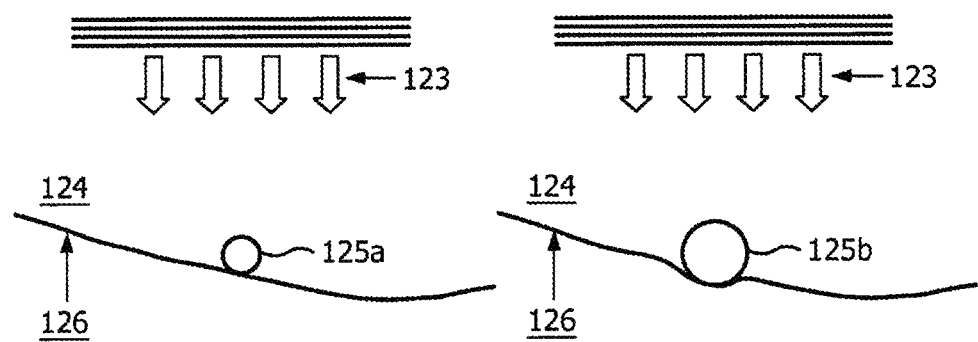
FIG. 7 illustrates the strain induced in the immediate vicinity of a VAR when subjected to ultrasonic oscillation.

FIG. 7 illustrates, in a schematic way, the conversion of acoustic pressure from an ultrasound wave 123 applied on a VAR 125a, 125b located within a vessel lumen 124, going from a compression phase 125a to an expansion phase 125b, to apply strain to the surface of a blood clot 126. This deformation is localized in the immediate vicinity of the VAR, does not occur elsewhere and causes a massaging effect believed to be associated with the promotion of flow restoration.

The high acoustic pressure levels facilitate clot lysis and vessel recanalization while minimizing detrimental bioeffects. These pressures are applied while focusing the ultrasound beam directly at the main clot or occlusion. Low acoustic pressures induce microvascular reperfusion with significantly lower microbubble disappearance rates than those at mid/high acoustic pressure. These low acoustic pressures are applied while focusing or directing the ultrasound beam in the volume surrounding the main occlusion to facilitate microvascular reperfusion, and allow the blood flow to replenish the various vessels in the proximity of the clot with additional microbubbles before continuing treatment with the higher pressure pulses. For instance, the low acoustic pressures can be applied by sequentially stepping differently steered ultrasound beams around the region surrounding the site of the occlusion.

FIGS. 3 and 5 illustrate spatial and temporal characteristics of exemplary VAR-mediated ultrasound treatment procedures in accordance with the present invention. Each of FIGS. 3a, 3b, 3c and 3d illustrate spatial distributions of pulsed ultrasound therapy beams in the treatment region in accordance with one implementation of the present invention. The left image of each pair of images shows the instantaneous pulse at a given time in the pulse sequence and the right image shows the accumulated pulse energy of the sequence. In the illustrated sequence the transducer array transmits a plurality of differently steered high pressure pulses directed at the site of the occlusion, followed by a plurality of differently steered low pressure pulses directed at the microvasculature surrounding the occlusion site. In FIG. 3a a first high pressure pulse is transmitted toward the occlusion site. This pulse is followed by three more high pressure pulses steered adjacent to the first pulse as illustrated by the four dark pulses at the center of the right image in FIG. 3b, in order to maximize the target area insonation on the clot. These four high pressure pulses are followed by low pressure pulses steered around the high pressure region as shown in FIG. 3b. In the right image it is seen that four low pressure pulses have been transmitted around the region exposed to high pressure pulses, starting at the three o'clock position and continuing to the six o'clock position by the time of FIG. 3b. This sequence of low pressure pulses continues in ever-expanding circles around the previous pulse locations as shown in FIG. 3c, where a second ring of low pressure pulses is nearing completion. Other, non-circular insonation patterns (i.e. raster scan pattern, random, outside-in, etc.) are also possible. Furthermore, the beam patterns of the low- and mid/high-pressure beams may be different, for example with a broader spatial distribution for the low-pressure beams than for the mid/high-pressure beam. The sequence continues until the entire region exposed to the low-pressure pulses has been insonified as shown in FIG. 3d. The spatial sequencing of relatively narrow pulses as opposed to a full floodlight insonation of the regions enables the practice of the present invention with the transducer arrays of many imaging probes without the need for mechanical scanning or a specially designed therapy/imaging probe by taking advantage of the probe's beam focusing and steering capabilities. For instance, as shown in the example of FIGS. 3a-3d, the pulses of the ultrasound waves at the mid/high and low acoustic pressure levels may have a diameter of about 3 mm. The pulsing can be performed rapidly enough to provide the necessary pressure for therapy while avoiding probe heating and the buildup of hazardous energy levels in the body in most instances.

Figure 5A:
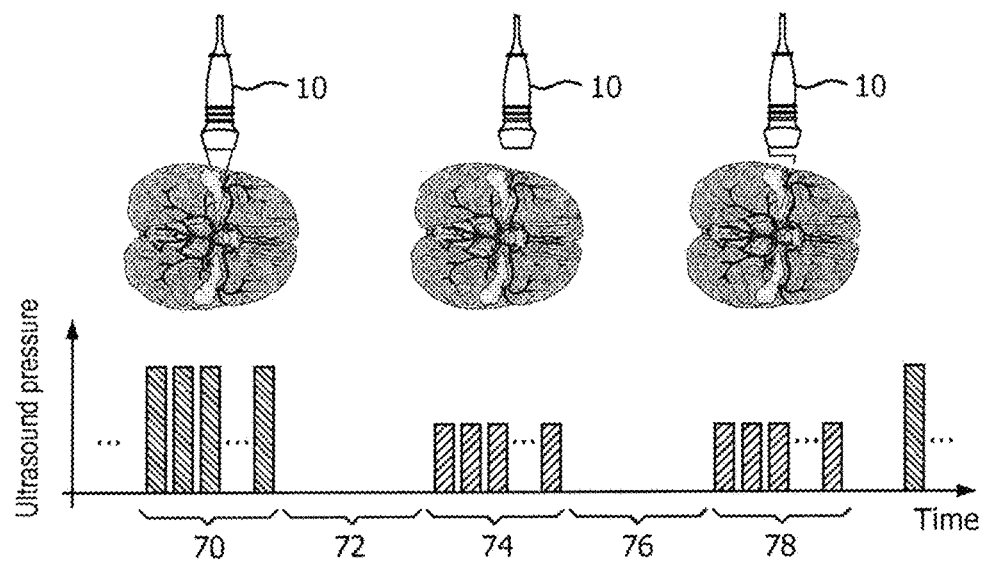
FIGS. 5a and 5b illustrate two treatment pulse sequences in accordance with the present invention.
Figure 5B:
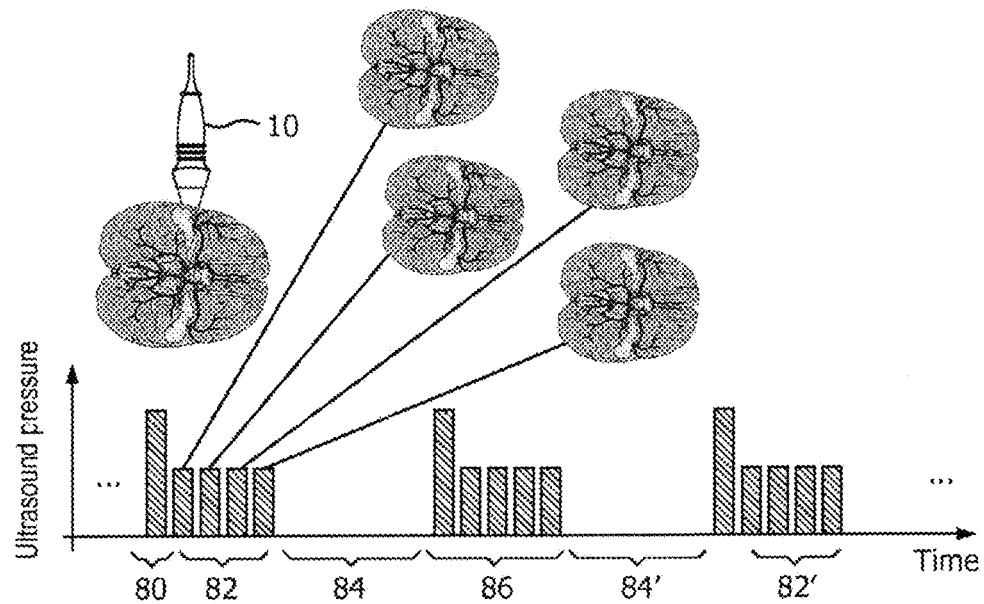

FIGS. 5a and 5b illustrate two other ultrasound treatment procedures in accordance with the present invention. The taller, dark bars in each drawing represent high level therapy pulses for clot lysis and the shorter, lighter bars represent low level therapy pulses for microvascular reperfusion stimulation. The treatment procedure of FIG. 5a begins with a sequence 70 of high pressure pulses directed at a clot to produce clot lysis. This is followed by a period 72 during which no therapeutic ultrasound waves are applied to allow microbubbles to replenish at the site of treatment. Optionally, imaging can be done at diagnostic levels during this time. Imaging at very low levels of mechanical index will have a minimal effect on VAR replenishment and enables the clinician to visualize the site of the therapy and assess the progress of clot lysis. Imaging is performed in a time-interleaved manner with ultrasonic therapy as described in international patent pub. no. WO 2008/017997 (Browning et al.) During the following interval 74 low level ultrasound pressure is delivered to the region surrounding the site of the occlusion (and may also overlap the occlusion site) to stimulate reperfusion in the surrounding microvasculature. Since this insonation is at low acoustic pressure, VAR replenishment can also occur during this interval. Interval 76 is another interval of no therapy to allow for maximal microbubble replenishment and, if desired, acquisition of one or more new 2D or 3D images of the treatment site. This is followed by another interval 78 of the delivery of low level ultrasound pressure to the surrounding microvasculature. After interval 78 the sequence repeats with another interval of high acoustic pressure therapy pulses.

For instance, the following parameters can be used for the treatment procedure of FIG. 5a, in combination with phospholipid-based gas-filled microbubbles: an ultrasonic frequency of 1 MHz for therapy pulses, a mid/high pressure level of about 200 kPa and a low pressure level of about 100 kPa (in-situ), a pulse duration of 2 milliseconds (msec) for each therapy pulse, and a microbubble replenishment interval of one second.

FIG. 5b illustrates another treatment procedure in which higher pressure therapy pulses are immediately followed by lower pressure pulses. One or more high pressure pulses are delivered to the site of an occlusion at time 80, followed by a plurality of differently steered low pressure pulses during the following interval 82. Each of the low pressure pulses are directed in a different direction through the surrounding microvasculature as illustrated in FIG. 3, thereby insonifying the full region subjected to the low pressure with a plurality of differently steered beams. The low pressure interval 82 is followed by a period 84 of no therapy pulses for microbubble replenishment during which imaging may optionally be performed. The sequence then repeats with another interval 86 of differently steered high pressure and low pressure pulses followed by another microbubble replenishment/imaging interval 84'. The sequence then continues in this manner until a satisfactory recanalization of the vessel is achieved, preferably with a substantially complete removal of the blood clot, which may optionally be followed by continued microvascular reperfusion stimulation. Typical parameters used for the treatment procedure of FIG. 5b are an ultrasonic frequency of 1 MHz for therapy pulses, a mid/high pressure level of 200 kPa or greater and a low pressure level of 80 kPa or less (in-situ), a pulse duration of 200 msec for high pressure pulses and 950 msec for each low pressure therapy pulse, and a microbubble replenishment interval of six seconds.

In other implementations the replenishment interval 72 or 84 may be omitted altogether, especially if ultrasound waves with low pressure pulses allows maintenance of a substantial amount of VAR at the site of therapeutic treatment, or if the successive pulses are sufficiently spaced apart in time, allowing the replenishment to occur during the application of ultrasound waves.

Other implementations will be readily apparent to those skilled in the art. For instance, instead of transmitting narrowly defined beams over a therapy region, an array transducer can be operated to produce floodlight insonation of the different regions of insonation. A high pressure beam can be formed and aimed at an occlusion to cause clot lysis, and a larger low pressure floodlight beam which insonifies the surrounding microvasculature can be formed and transmitted to stimulate microvascular reperfusion with a single broad beam as illustrated in FIG. 2.

In a preferred embodiment, therapy and imaging are alternately performed and imaging is done while therapy is suspended for the unimpeded flow of fresh microbubbles to the site of an occlusion. Referring to FIG. 1, according to a preferred embodiment, the transducer arrays 10a and 10b transmit ultrasonic waves into the cranium of a patient from opposite sides of the head, although other locations may also or alternately be employed such as the front of the head or the sub-occipital acoustic window at the back of the skull. The sides of the head of most patients advantageously provide suitable acoustic windows for transcranial ultrasound at the temporal bones around and above the ears on either side of the head. Suitable headsets for cranial ultrasound transducers are described in previously mentioned international patent publication no WO 2008/017997 (Browning et al.), US pat. pub. no. US 2012/0083718 (Alleman et al.), and US pat. pub. no. US 2011/0251489 (Zhang et al.), for instance.

The aforementioned Browning et al. application shows a headset with two transducer arrays acoustically coupled to opposite sides of the head. Each transducer array can image the side of the brain closest to the array to search for a thrombus, then deliver acoustic energy to treat a located thrombus. A thromboembolic occlusion that causes stroke most often occurs in the region of the proximal middle cerebral artery (MCA) that is very close to the brain midline. Less frequently, such an occlusion can occur much closer to the ipsilateral temporal bone, in the distal MCA or other regions away from the brain midline. VARs generally flow toward the occluded region in the blood stream and, due to the geometry of the brain and its vasculature, the blood flow in the MCA is directed from the brain midline toward the ipsilateral temporal bone. Thus, the flow of fresh VARs to the site of an occlusion is generally toward the temple where the headset transducer closest to the occlusion is located. As a result, acoustic waves from the ipsilateral transducer can have the effect of opposing the desired flow of fresh VARs toward the thrombus. In order for effective thrombus dissolution, it is desirable for VARs to be present in the treatment region, move close to the surface of the occluding thrombus, or even penetrate into the occluding thrombus itself. In accordance with the principles of the present invention, this is achieved or, minimally, enhanced by using the mechanism of acoustic radiation force, which acts on the VARs by pushing them along in the direction of the ultrasound propagation. Because of the vessel geometry in the brain, in order for the acoustic radiation force to push VARs into the occlusion, it is necessary for the ultrasound "pushing" array to be placed on the contralateral temporal bone. The contralateral array produces ultrasound beams that propagate from the contralateral to the ipsilateral side, thereby pushing the VARs toward the occlusion. The radiation force can not only push VARs to move toward the initial occlusion clot, but also push them closer to the clot or even inside the clot for more effective lysis. In addition, the radiation force may help VARs move (with the synergistic assistance of pulsatile blood pressure, possibly in an oscillating, forward, peristaltic motion) into the entire occlusive region, including the initial occlusion site and any subsequently occluded or resultant ischemic downstream vascular space. The greater the degree of flow obstruction, the smaller the supply of fresh resonator-containing blood to the occlusion site as well as its downstream vascularity. The pulsatile blood pressure can push VARs closer to the clot surface, as well as to move into the space of the downstream vasculature. Accordingly it is desirable to be able to promote the flow/motion of new resonators both to the initial occlusion site as well as its downstream vascular space to enhance the lysis effect of VARs that are close to or inside the occluded vascular space.

Figure 8:
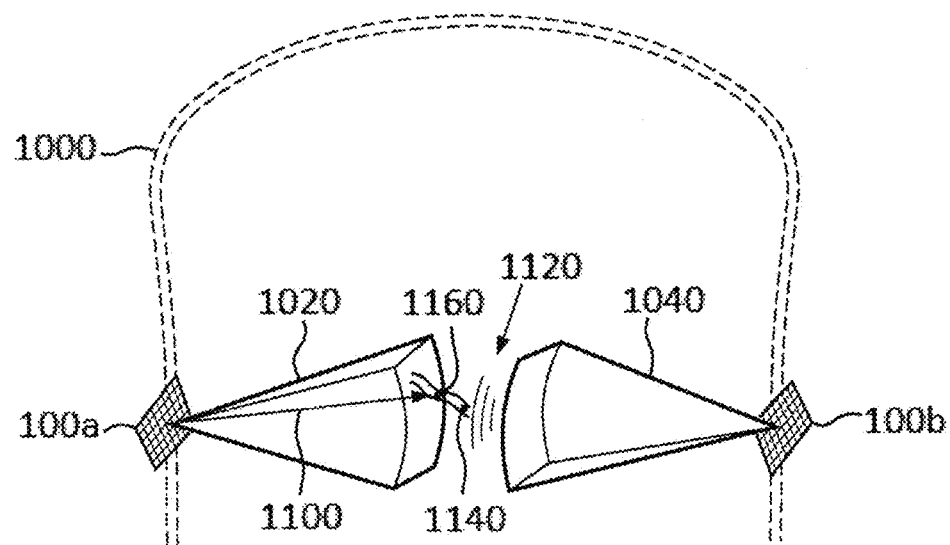
FIG. 8 illustrates stroke treatment with a two-transducer headset in accordance with the present invention.

This is illustrated in FIG. 8, in which the ultrasound system of FIG. 1 is used to apply sonothrombolysis therapy and concurrently urge a flow of fresh VARs to the therapy site in a time interleaved manner. For stroke treatment the transducer arrays 100a, 100b are preferably not employed in conventional ultrasound probes, but are custom probes built into a headset and placed on the temporal bone windows of a stroke victim as shown in FIG. 8. The two transducer arrays of the headset will position themselves against the temporal bone acoustic windows on both sides of the skull 1000 as shown in the illustration. When positioned this way, the acoustic fields of the arrays are generally oriented towards the MCA region toward the center of the brain. In this example, the ipsilateral side where a clot 1160 is located is within the therapy beam steering region 1020 of transducer array 100a. A therapy beam 1100 can be steered in three dimensions within this region 1020 and directed at a thrombus 1160 for therapy as shown in the illustration. A similar region 1040 exists in front of the contralateral transducer 100*b* on the other side of the head. However the ultrasonic energy produced by the contralateral transducer 100*b* is not at a therapeutic level but at a lower level which produces ultrasonic energy waves 1120 which are sufficient to promote a gentle acoustic radiation force on VARs in the blood vessel 1140 leading to the thrombus 1160. Preferably this is done with low acoustic pressure that is insufficient to disrupt or rupture the VARs as the higher energy therapeutic beam does, but is only sufficient to promote the movement of the VARs in vessel 1140 toward the clot 1160. The contralateral transducer array 100*b* could be used for therapy. But the greater distance from the contralateral temporal bone to the occlusion 1016 as compared to that from the ipsilateral temporal bone to the occlusion means that ultrasound pulses with greater pressure amplitude would be needed to be transmitted for therapy from the contralateral side than from the ipsilateral side, to account for the increased signal attenuation due to the longer beam path length. The greater pressure amplitude implies the use of an ultrasound array with a larger aperture for producing a high intensity focused beam reaching a greater distance from the array. However, the effective aperture of the array is typically limited by the size of the particular temporal acoustic window. In addition, it is desirable to use identical transducer arrays with identical apertures for uniformity of operation regardless of the thrombus location. Therefore, it is advantageous to deliver the therapeutic ultrasound pulses from the ipsilateral side transducer array 100*a*, where the therapeutic beams have a shorter distance to traverse to reach the site of the thrombus 1160. Thus, it is advantageous in an implementation of the present invention to use contralateral ultrasound beams to generate the acoustic radiation force needed to push the VARs towards the occluding thrombus, and ipsilateral beams for the delivery of the therapeutic ultrasound pulses to actually lyso the clot. Various electronic configurations can be used to actuate the opposing transducer arrays. Both arrays can be driven alternatively by multiplexing the same electronics, or the array (operated for imaging and radiation force) on the contralateral side and the array (operated for therapy) on the ipsilateral side may be driven simultaneously by two separate signal generators and power amplifiers.

In practice of the method of the present invention an IV would be started to later deliver the VARs and the location of the clot could be determined by MR, CT, or ultrasound imaging. The VAR mediation can be provided by a systemically infused dose of a VAR contrast agent circulating throughout the entire blood stream and capable of reaching the occluded region via residual and collateral flow. The VARs will remain substantially intact at low ultrasound pressure levels, will provide increased clot lysis capability at mid-pressure levels, and will replenish the treatment region throughout the entire sonothrombolysis therapy procedure during the periods of non/low amplitude insonification.

When the same transducer array 100*a*, 100*b* is used for diagnosis and therapy it can be used to locate the clot itself via the absence of blood flow and/or perfusion distal to the site of the clot occlusion, using the low-MI ultrasound contrast imaging or Doppler techniques already in use. Once a clot has been located in a blood vessel, mid- or high-pressure beams are produced by the ipsilateral array transducer which are aimed at the general clot location. Typical penetration distance requirements are approximately 3-10 cm from the skull surface. Typical 3D beam steering angle requirements are approximately up to ±27°, and focal zone size requirements for treatment are approximately 5-10 mm in diameter. The ultrasonic output of the array transducer should be sufficient to generate both mid-pressure and low-pressure pulses inside the brain, further accounting for temporal bone attenuation, which attenuates the beam by approximately 75%.

In an implementation of the present invention operating at 1 MHz, an in-situ pressure of approximately 140 to 250 kPa is needed for a phospholipid-based microbubble agent to undergo stable cavitation in the brain. Periodically, the transmission of therapy beams by the ipsilateral transducer array is interrupted to allow a fresh supply of microbubbles to flow to the thrombus. During this time the contralateral transducer array is actuated to transmit low acoustic pressure levels toward the therapy site, e.g., between approximately 80 and 140 kPa, with the effect of providing acoustic pushing pulses which urge fresh microbubbles toward and into the thrombus. This low level ultrasonic stimulation can also provide the beneficial effect of inducing microvascular reperfusion as described herein. The low level ultrasound used to urge the microbubbles toward the clot can also be used to image the site of the clot from the contralateral side of the head if desired. Ultrasound imaging is preferably employed by either transducer array to image microbubble reperfusion during pauses in the treatment, to observe the progress of clot lysis, and to observe the presence and flow of microbubbles to the site of the occlusion and surrounding microvasculature. Therapeutic ultrasound exposure is resumed once a sufficiently high amount of microbubbles have re-perfused the target region after microbubble destruction with the stimulus of the contralateral acoustic radiation force.

Figure 9:
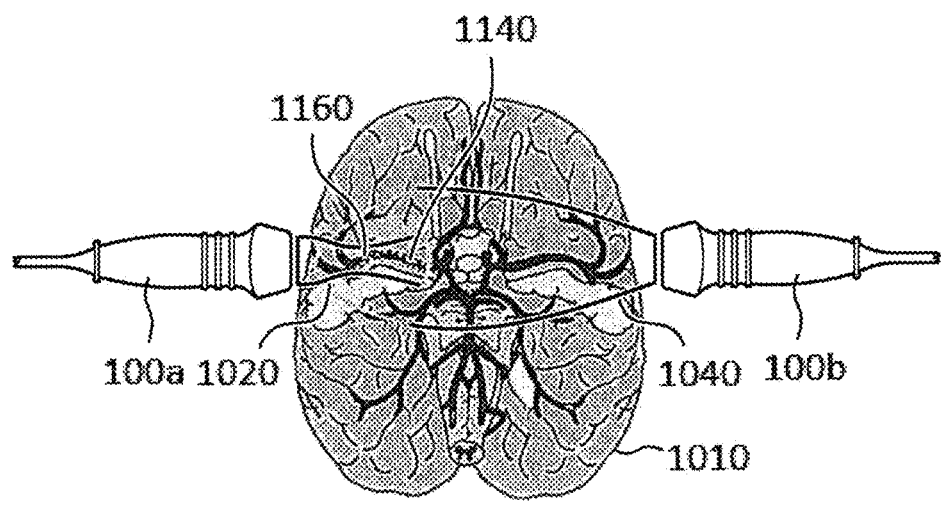
FIG. 9 is an anatomical illustration of the delivery of acoustic radiation force and sonothrombolytic treatment for stroke in accordance with the principles of the present invention.

FIG. 9 is an anatomical illustration of stroke sonothrombolysis therapy being applied from an acoustic window at the left side of the head which is alternated with acoustic radiation force from the other side of the head to urge microbubbles 1140 toward a cranial thrombus 1160. The transducer probe 100*a* used for therapy in this example is seen located at the acoustic window of the temple on the left side of the head where it insonifies the brain 1010 from the ipsilateral side where the thrombus is located. The narrow hourglass-shaped energy profile 1020 of mid- to high-energy ultrasound is seen to be focused at the depth of the blood clot 1160 in the middle cerebral artery (MCA). Located at the acoustic window of the right temple of the head, the contralateral side, in this example, is another transducer probe 100*b*. The broader energy profile 1040 produced by transducer probe 100*b* provides low energy acoustic radiation force toward the ipsilateral MCA, urging the VARs 1140 toward the blood clot 1160. Preferably high energy clot-disrupting therapy and low energy radiation force urging of the VARs are alternated periodically, as it can be seen that the pressure waves from the two transducer probes are directed in opposite directions and the resulting radiation forces would otherwise oppose each other. During the periods of low energy radiation force pushing of the VARs towards 1160 imaging is performed of the therapy site by one of the probes so that the clinician can assess the progress of the therapy and observe a build-up of fresh VARs in proximity to the thrombus 1160 before resuming therapy.

It has been found that in order to achieve effective in-situ pressures with phospholipid-based VARs, approximately 140 to 250 kPa of acoustic pressure is needed. This higher pressure level facilitates clot lysis and vessel recanalization while minimizing detrimental bioeffects. These pressures are applied while focusing the ultrasound beam directly at the main clot/occlusion. Lower pressures at approximately 140 kPa (or lower) at 1 MHz, are used for acoustic radiation force push pulses and inducing microvascular reperfusion with significantly lower microbubble destruction rates. These lower pressures are applied while focusing the ultrasound beam more broadly as shown in FIG. 9. Pressures below these levels, for example on the order of 50 kPa, are those that may also stimulate microvascular reperfusion but are less effective at 1 MHz to push microbubbles towards the thrombus. In general, microbubbles of different sizes respond differently to various pressures, and lower pressures will destroy fewer microbubbles while higher pressures will destroy more.

While relatively lower frequency ultrasound is more effective for clot lysis, relatively higher frequency ultrasound is more effective for generating greater radiation force and in addition inducing less microbubble destruction. Therefore, low-intensity, long ultrasound tonebursts at a relatively higher frequency are preferred for the effective generation of non-destructive radiation force from the contralateral transducer. Other pulse types such as chirps or amplitude modulated tone-bursts may also be employed for producing pulsatile radiation forces which are effective for pushing microbubbles of different sizes.

In accordance with embodiments herein, the present invention provides an ultrasonic sonothrombolysis system that includes two array transducers each acoustically coupled to an acoustic window on opposite sides of the head of a subject; and a transmit controller, coupled to control the transmission of ultrasound by the two array transducers, and operated to cause an ipsilateral one of the array transducers to direct high energy ultrasound to the site of an occlusion and to cause a contralateral one of the array transducers to direct low energy ultrasound to a blood vessel supplying microbubbles to the site of the occlusion. The contralateral array transducer produces an acoustic radiation force for urging microbubbles toward the occlusion. The transmit controller can be further adapted to produce high energy and low energy ultrasound transmission by the two array transducers in a time-interleaved sequence. The transmit controller can further cause the ipsilateral array transducer to produce ultrasound which is narrowly focused at the occlusion, and cause the contralateral array transducer to produce ultrasound which is more broadly focused at the site of the occlusion and surrounding vasculature. In some embodiments, the ipsilateral array transducer directs therapy beams to the site of an occlusion from one side of the head and the contralateral transducer directs an oppositely directed acoustic radiation force from the other side of the head. The acoustic windows can further include the temples on opposite sides of the head. The transmit controller can further cause one of the array transducers to perform ultrasound imaging of the site of the occlusion during periods of low energy ultrasound transmission. In some embodiments, the transmit controller is further adapted to cause the ipsilateral array transducer to produce high energy insonification sufficient to cause inertial cavitation at the site of the occlusion and to cause the contralateral array transducer to produce low energy insonification sufficient to cause stable cavitation at the site of the occlusion. In certain embodiments, the transmit controller is adapted to produce high pressure insonification of at least 180 kPa and low level pressure insonification of not greater than 140 kPa.

The present invention further provides a method of providing sonothrombolysis to a site of a vascular occlusion. The method can include controlling an ipsilateral array transducer which is acoustically coupled to one side of a head to direct high energy ultrasound to the site of an occlusion; and controlling a contralateral array transducer which is acoustically coupled to the other side of the head to direct low energy acoustic radiation force ultrasound to the site of the occlusion to stimulate flow of microbubbles toward the occlusion. The high energy and low energy ultrasound can be provided in a time-interleaved sequence. In some embodiments, the controlling the ipsilateral array transducer to direct high energy ultrasound to the site of an occlusion can include producing ultrasound pressure levels which are at least capable of causing stable cavitation, and controlling the contralateral array transducer to direct low energy ultrasound to the site of the occlusion can include producing ultrasound pressure levels not greater than those capable of causing stable cavitation. The method can also include controlling the ipsilateral array transducer to cease production of high energy ultrasound during a microbubble replenishment interval, in which the contralateral array transducer produces acoustic pushing pulses during the microbubble replenishment interval. In some embodiments, the method can include controlling one of the array transducers to perform diagnostic imaging of the site of the occlusion during the microbubble replenishment interval. The method can include controlling the ipsilateral array transducer to perform diagnostic imaging of the site of the occlusion during the microbubble replenishment interval. In some embodiments, the high energy ultrasound is at a relatively low frequency, and the low energy ultrasound is at a relatively high frequency.

The invention claimed is:

1. An ultrasound stroke treatment system comprising:
   at least one array transducer, wherein the at least one array transducer is arranged to selectively produce insonation at a mid/high acoustic pressure level by transmitting mid/high pressure ultrasound pulses at the mid/high acoustic pressure level, and at a low acoustic pressure level by transmitting low pressure ultrasound pulses at the low acoustic pressure level; and
   a transmit controller circuit coupled to the array transducer, wherein the transmit controller circuit is arranged to control the transmission of the mid/high pressure ultrasound pulses and the low pressure ultrasound pulses by the at least one array transducer,
   wherein the transmit controller circuit is arranged to perform a treatment application by causing the at least one array transducer to direct at least one of the mid/high pressure ultrasound pulses to a site of an occlusion during a first therapy time interval and to steer the low pressure ultrasound pulses to different locations sequentially expanding from the at least one of the mid/high pressure ultrasound pulses in a region adjacent to and completely surrounding the site of the occlusion during a second reperfusion stimulation treatment time interval, and
   wherein the insonation by the mid/high pressure ultrasound pulses stimulates clot lysis and the insonation by the low pressure ultrasound pulses stimulates microvascular reperfusion of tissue in the region adjacent to and surrounding the site of the occlusion both in the presence of vascular acoustic resonators (VARs).

2. The ultrasound stroke treatment system of claim 1, wherein the transmit controller circuit is further configured to produce the insonation at the mid/high acoustic pressure level and at the low acoustic pressure level simultaneously.

3. The ultrasound stroke treatment system of claim 2, wherein the transmit controller circuit is further configured to steer the low pressure ultrasound pulses to sequentially surround the at least one of the mid/high pressure ultrasound pulses by sequentially transmitting the low pressure ultrasound pulses in different directions through the tissue surrounding the site of the occlusion.

4. The ultrasound stroke treatment system of claim 3, wherein the transmit controller circuit is further configured to direct the at least one of the mid/high pressure ultrasound pulses by sequentially transmitting the mid/high pressure ultrasound pulses in different directions proximate to the site of the occlusion.

5. The ultrasound stroke treatment system of claim 1, wherein the transmit controller circuit is further configured to suspend both the insonation at the mid/high acoustic pressure level and the insonation at the low acoustic pressure level during a third time interval to enable VAR replenishment in the region adjacent to and surrounding the site of the occlusion.

6. The ultrasound stroke treatment system of claim 5, wherein the transmit controller circuit is further configured to perform diagnostic imaging during the third time interval, wherein an acoustic pressure level of insonation for the diagnostic imaging does not exceed the low acoustic pressure level during the third time interval.

7. The ultrasound stroke treatment system of claim 1, wherein the transmit controller circuit is further configured to operate at a frequency of 1 MHz to produce the insonation at the mid/high acoustic pressure level greater than 140 kPa in situ and the insonation at the low acoustic pressure level of not greater than 140 kPa in situ.

8. The ultrasound stroke treatment system of claim 1, wherein the VARs comprise gas-filled microvesicles.

9. The ultrasound stroke treatment system of claim 1, further comprising:
an ipsilateral array transducer probe comprising the at least one array transducer, wherein the at least one array transducer is configured to produce insonation at the mid/high acoustic pressure level and the ipsilateral array transducer probe is configured to position the at least one array transducer so as to direct therapy beams to the site of the occlusion from one side of a patient's head; and
a contralateral transducer probe comprising another of the at least one array transducer configured to produce insonation at the low acoustic pressure level, wherein the contralateral transducer probe is configured to position the another of the at least one array transducer so as to direct an oppositely directed acoustic radiation force from an opposite side of the patient's head.

10. The ultrasound stroke treatment system of claim 1, wherein the transmit controller circuit is further configured to direct the mid/high pressure ultrasound pulses over a pulse duration between 5 to 50 milliseconds.

11. The ultrasound stroke treatment system of claim 1, wherein the transmit controller circuit is further configured to steer the low pressure ultrasound pulses in a circular insonation pattern surrounding the site of the occlusion to which the at least one of the mid/high pressure ultrasound pulses is directed.

12. The ultrasound stroke treatment system of claim 1, wherein the transmit controller circuit is further configured to cause the at least one array transducer to direct the mid/high pressure ultrasound pulses sequentially to different locations at the site of the occlusion.

13. The ultrasound stroke treatment system of claim 1, wherein the mid/high pressure ultrasound pulses and the low pressure ultrasound pulses have a diameter of about 3 mm.

14. The ultrasound stroke treatment system of claim 1, wherein the transmit controller circuit is further configured to produce the insonation at the mid/high acoustic pressure level and at the low acoustic pressure levels in a time-interleaved sequence.

15. The ultrasound stroke treatment system of claim 1, wherein the transmit controller circuit is further configured to steer the low pressure ultrasound pulses in a non-circular insonation pattern surrounding the site of the occlusion to which the at least one of the mid/high pressure ultrasound pulses is directed.

* * * * *